(12) United States Patent
Lee et al.

(10) Patent No.: US 8,297,284 B2
(45) Date of Patent: Oct. 30, 2012

(54) AUXILIARY DEVICE FOR AN AEROSOL THERAPY UNIT

(75) Inventors: Gary C. J. Lee, I-Lan (TW); Shu-Ping Zou, Taipei (TW); Yi-He Lee, Taipei (TW)

(73) Assignee: Galemed Corporation, I-Lan (TW)

( * ) Notice: Subject to any disclaimer, the term of this patent is extended or adjusted under 35 U.S.C. 154(b) by 793 days.

(21) Appl. No.: 12/484,770

(22) Filed: Jun. 15, 2009

(65) Prior Publication Data

US 2010/0000525 A1    Jan. 7, 2010

(30) Foreign Application Priority Data

Jul. 1, 2008 (TW) ............................... 97124704 A

(51) Int. Cl.
*A61M 16/06* (2006.01)
(52) U.S. Cl. .............................. 128/207.13; 128/200.26
(58) Field of Classification Search . 128/202.12–202.13, 200.26, 207.14–207.18
See application file for complete search history.

(56) References Cited

U.S. PATENT DOCUMENTS

| 4,622,034 A * | 11/1986 | Shattuck ...................... 604/179 |
| 4,941,434 A * | 7/1990 | Ellwanger ..................... 119/771 |
| 5,064,122 A | 11/1991 | Kamishita et al. |
| 5,375,593 A | 12/1994 | Press |
| 5,462,050 A | 10/1995 | Dahlstrand |
| 5,904,140 A | 5/1999 | McGoogan |
| 6,068,649 A * | 5/2000 | Chamberlain ................ 606/234 |
| 6,247,470 B1 | 6/2001 | Ketchedjian |
| 6,948,494 B1 * | 9/2005 | Snow ....................... 128/203.15 |
| 7,020,936 B2 * | 4/2006 | Tsai ................................ 24/302 |
| 7,063,084 B2 * | 6/2006 | McDonald ............... 128/200.28 |
| 7,631,399 B2 * | 12/2009 | Soumi ......................... 24/115 R |
| 2006/0048346 A1 | 3/2006 | Soumi |
| 2009/0320851 A1 * | 12/2009 | Selvarajan et al. ...... 128/207.13 |

FOREIGN PATENT DOCUMENTS

CN    201082290 B1    7/2008
* cited by examiner

*Primary Examiner* — Stephen Crow

(57) ABSTRACT

An auxiliary device for an aerosol therapy unit includes a main body and a delivery tube. The main body includes a nose mask portion having a tube connector with an inlet hole, and a nipple-connecting portion connected integrally to and disposed below the nose mask portion. The delivery tube has one end connected to the inlet hole, and the other end adapted to be connected to a source of medication or gas.

10 Claims, 7 Drawing Sheets

AUXILIARY DEVICE FOR AN AEROSOL THERAPY UNIT

CROSS-REFERENCE TO RELATED APPLICATION

This application claims priority of Taiwanese Application No. 097124704, filed on Jul. 1, 2008.

BACKGROUND OF THE INVENTION

1. Field of the Invention

This invention relates to an auxiliary device for an aerosol therapy unit.

2. Description of the Related Art

Referring to FIG. 1, a conventional oxygen delivery device 1 generally has a transparent soft tube 11, and a pair of prongs 12 projecting from and communicating fluidly with the soft tube 11. In use, a medical professional cuts the soft tube 11 to a suitable length according to the size of a patient's face, after which two opposite ends of the soft tube 11 are connected respectively to an air inlet and an air outlet of an oxygen supply device (not shown) through two conduits 13, 14, respectively. The prongs 12 are disposed toward the patient's nostrils. Further, pieces of adhesive tape are used to position the soft tube 11 and the prongs 12 on the patient's face. Oxygen flows into the patient's nostrils through the prongs 12.

However, the conventional oxygen delivery device 1 is inconvenient to use since the length of the soft tube 11 must be cut prior to use, and adhesive tape must be used to position the soft tube 11 and the prongs 12 on the patient's face. Further, streams of air flowing through the prongs 12 into the patient's nostrils can make the patient feel uncomfortable. Moreover, the soft tube 11 and the prongs 12 may appear intimidating to small children and infants, so that it is difficult to position the conventional oxygen delivery device 1 on the face of a small child or infant.

A medical pacifier, as disclosed in U.S. Pat. No. 5,904,140, resolves the aforementioned drawbacks, and comprises a tubular body including a wall defining a hollow interior having an inlet connected to a nebulizer to receive air-entrained medication, and a closed end mounted to a stopper which carries a nipple. The wall further has a discharge port adjacent the closed end of the hollow interior. A deflector is mounted to the wall in a position partially overlying the discharge port. When the air-entrained medication exits from the hollow interior of the body through the discharge port, it is directed by the deflector toward the nostrils of an infant sucking on the nipple.

SUMMARY OF THE INVENTION

Therefore, the object of the present invention is to provide a novel auxiliary device for an aerosol therapy unit.

According to this invention, an auxiliary device for an aerosol therapy unit comprises a main body and a delivery tube. The main body includes a nose mask portion having a tube connector with an inlet hole, and a nipple-connecting portion connected integrally to and disposed below the nose mask portion. The delivery tube has one end connected to the inlet hole, and the other end adapted to be connected to a source of medication or gas.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
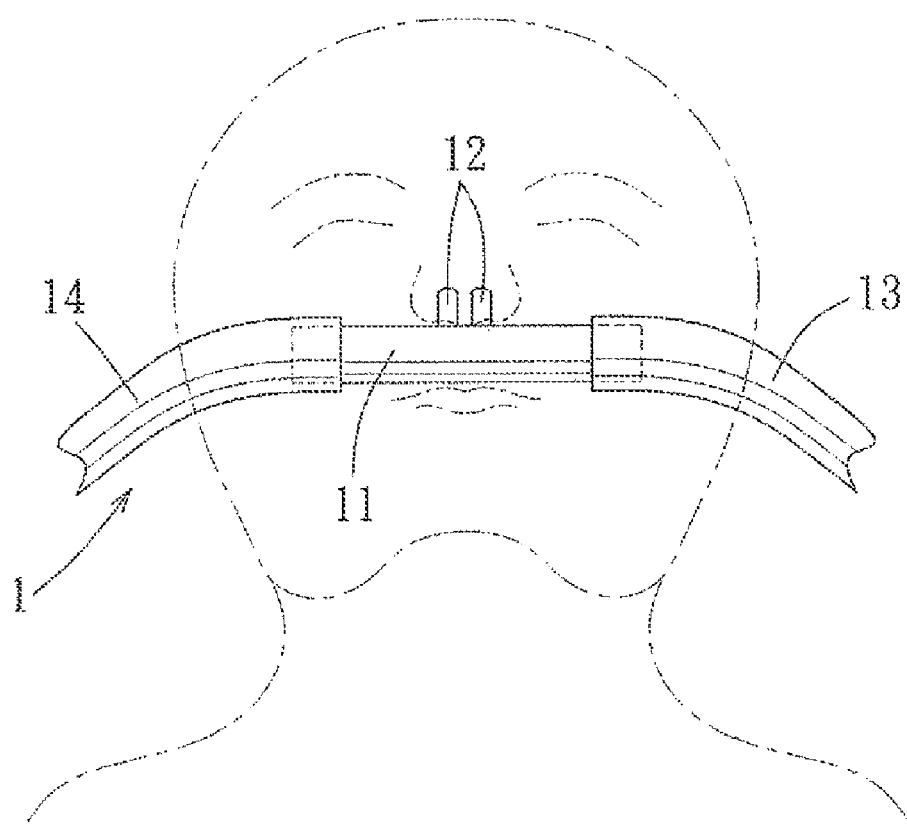
FIG. 1 is a schematic view of a conventional oxygen delivery device in a state of use.

Before the present invention is described in greater detail, it should be noted that the same reference numerals have been used to denote like elements throughout the specification.

Referring to FIGS. 2 to 5, an auxiliary device 4 for an aerosol therapy unit according to the first preferred embodiment of the present invention is shown to comprise a main body 21, a bendable retention plate 22, a nipple unit 3, and a delivery tube 5.

Figure 2:
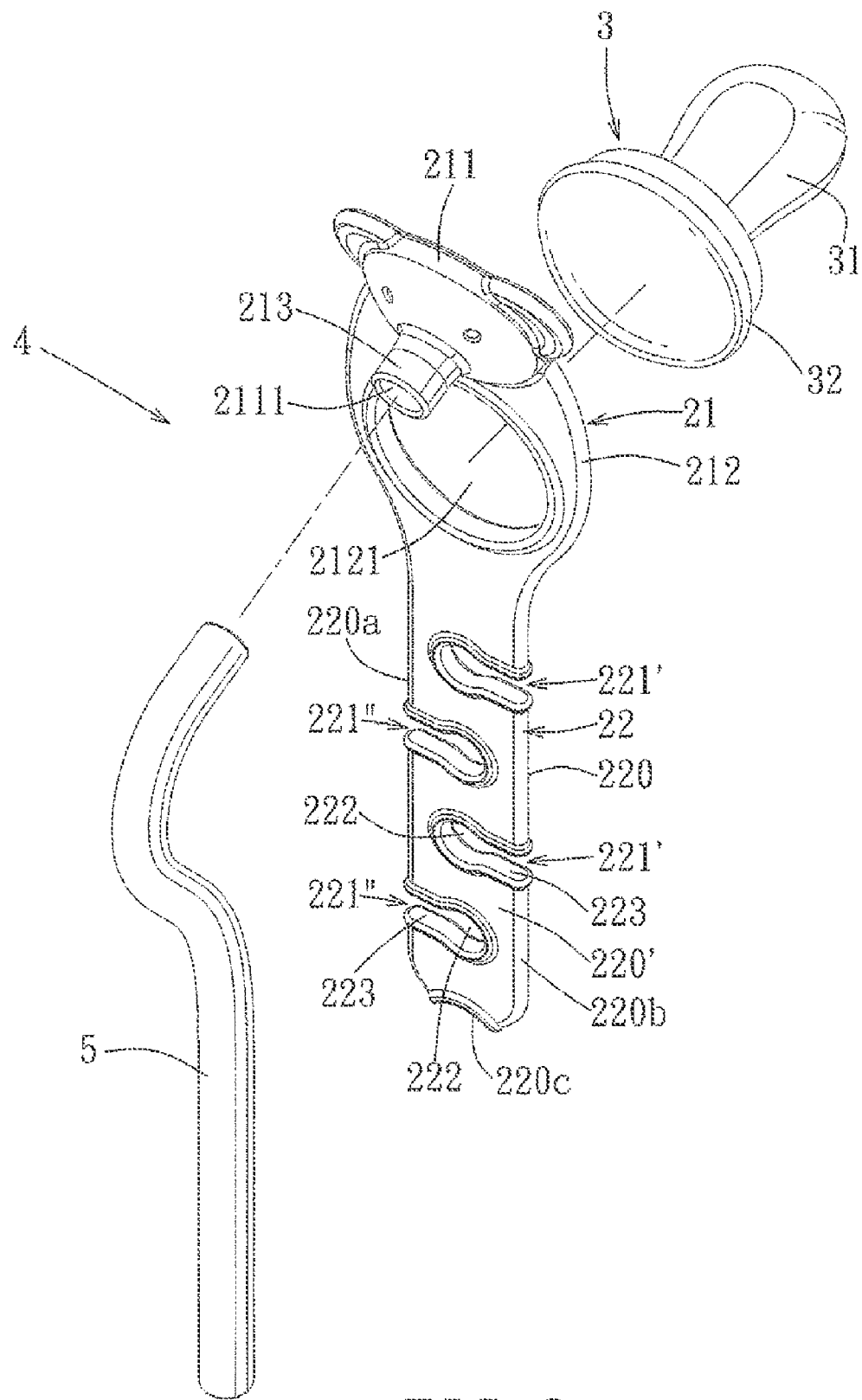
FIG. 2 is an exploded perspective view of an auxiliary device for an aerosol therapy unit according to the first preferred embodiment of this invention.
Figure 3:
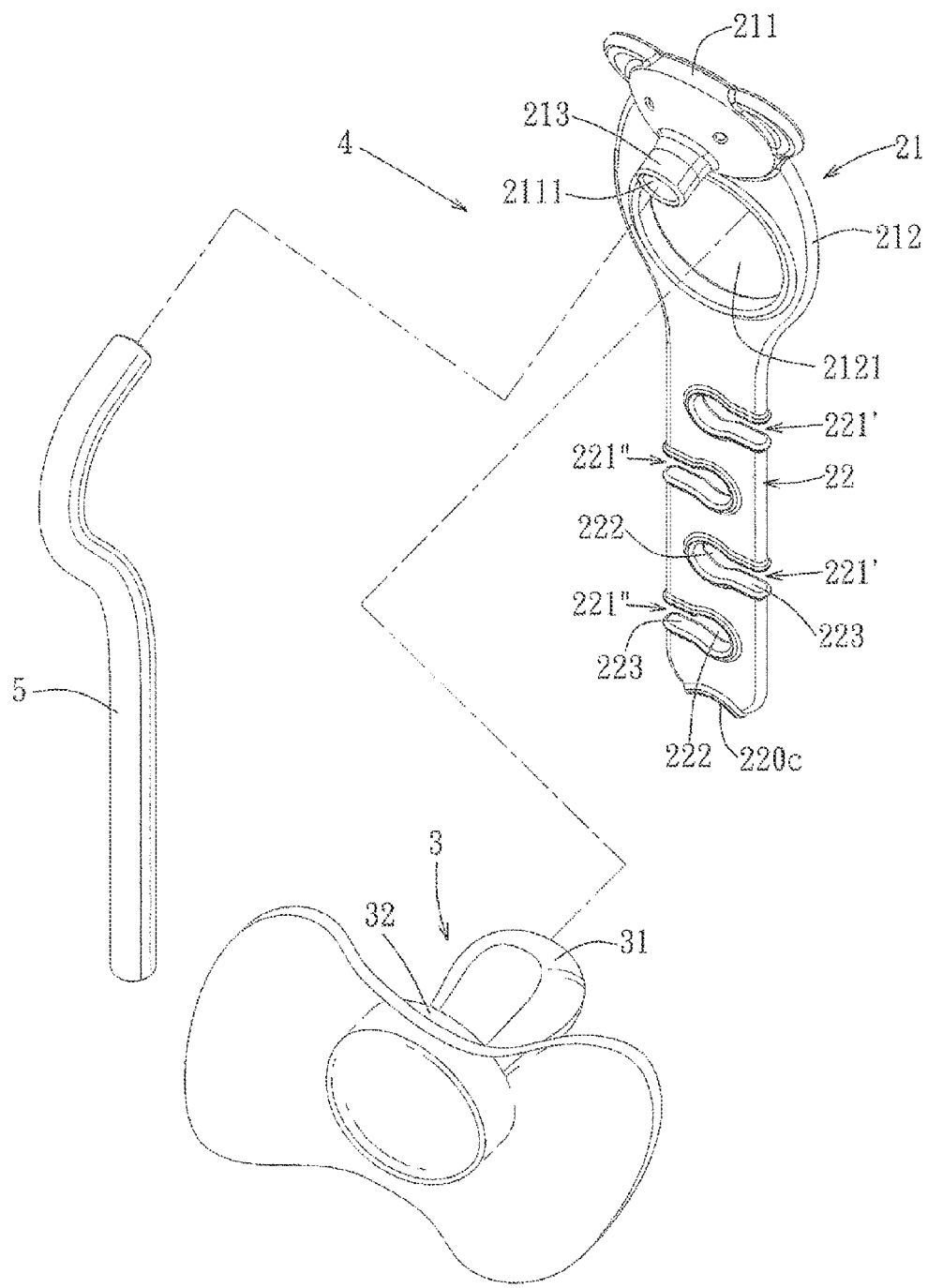
FIG. 3 is a view similar to FIG. 2, but illustrating an alternative form of a nipple unit of the first preferred embodiment.
Figure 5:
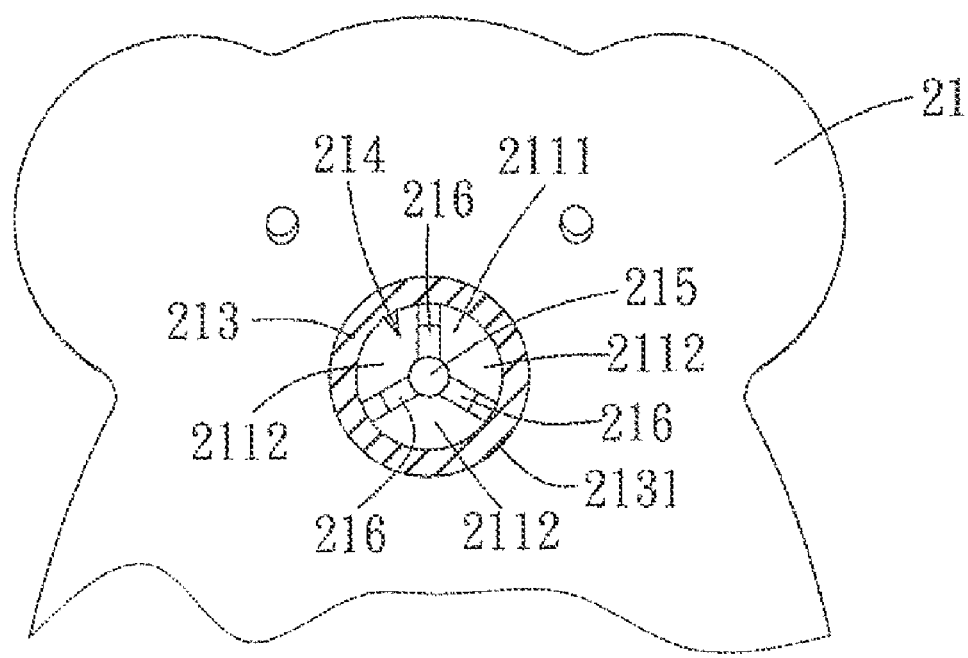
FIG. 5 is a sectional view of the first preferred embodiment taken along line V-V of FIG. 4.

The main body 21 includes a nose mask portion 211 having a tube connector 213, and a nipple-connecting portion 212 connected integrally to and disposed below the nose mask portion 211 and having a connecting hole 2121. The connecting hole 2121 may be a through hole, as shown in FIG. 2, or a blind hole (not shown). In this embodiment, the connecting hole 2121 is a through hole. The nose mask portion 211 may be provided in a shape so as to be more acceptable to infants and small children. In this embodiment, the nose mask portion 211 has a shape of a bear's head. With particular reference to FIG. 5, the tube connector 213 has a tube wall 2131 confining an inlet hole 2111 for passage of a flow current of an aerosolized medication or gas therethrough. The main body 21 further includes a flow-damping unit 214 provided transversely within the inlet hole 2111 and adapted to dampen the flow current passing through the inlet hole 2111. The flow-damping unit 214 has a central portion 215, and a plurality of angularly spaced-apart ribs 216 projecting radially from the central portion 215 to the tube wall 2131 so as to divide the inlet hole 2111 into a plurality of hole sections 2112.

The bendable retention plate 22 extends downwardly from the nipple-connecting portion 212, and has an inner face 220 adapted to face a user, an outer face 220' opposite to the inner face 220, left and right sides (220a, 220b), and a bottommost push end (220c). The retention plate 22 is provided with a plurality of retaining elements that are spaced apart from each other along the length of the retention plate 22. The retaining elements are configured as passage holes extending through the inner and outer faces 220, 220' of the retention plate 22. In this embodiment, the passage holes include alternating first and second passage holes 221', 221". Each of the first and second passage holes 221', 221" has a large hole portion 222, and a small hole portion 223 communicating spatially with the large hole portion 222. The small hole portions 223 of the first passage holes 221' open at the right side (220b) of the retention plate 22. The small hole portions 223 of the second passage holes 221" open at the left side (220a) of the retention plate 22.

The nipple unit 3 is connected detachably to the nipple-connecting portion 212, and has a nipple portion 31 extending through the connecting hole 2121, and an insert portion 32 opposite to the nipple portion 31. Since the main body 21 and the nipple unit 3 are made of flexible materials, an inner diameter of the connecting hole 2121 may be smaller than a largest diameter of the insert portion 32, so that when the nipple portion 31 extends through the connecting hole 2121, the insert portion 32 is resiliently and detachably clamped by a wall that confines the connecting hole 2121, thereby securely positioning the nipple unit 3 on the nipple-connecting portion 212 of the main body 21. It should be noted that the nipple unit 3 may be a pacifier to enhance the feeling of comfort and familiarity for the infant or small child.

Figure 4:
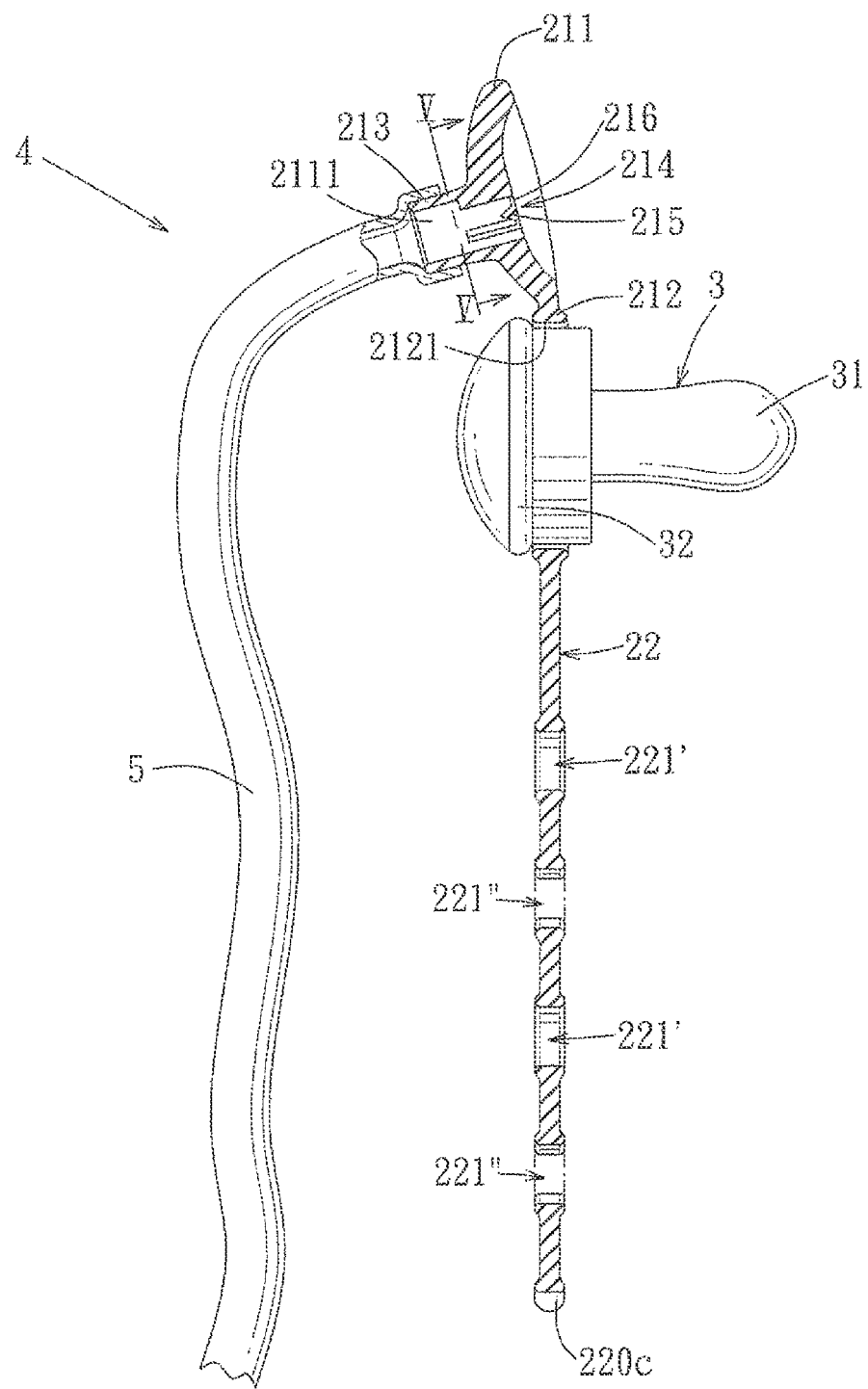
FIG. 4 is a sectional view of the first preferred embodiment in an assembled state.
Figure 6:
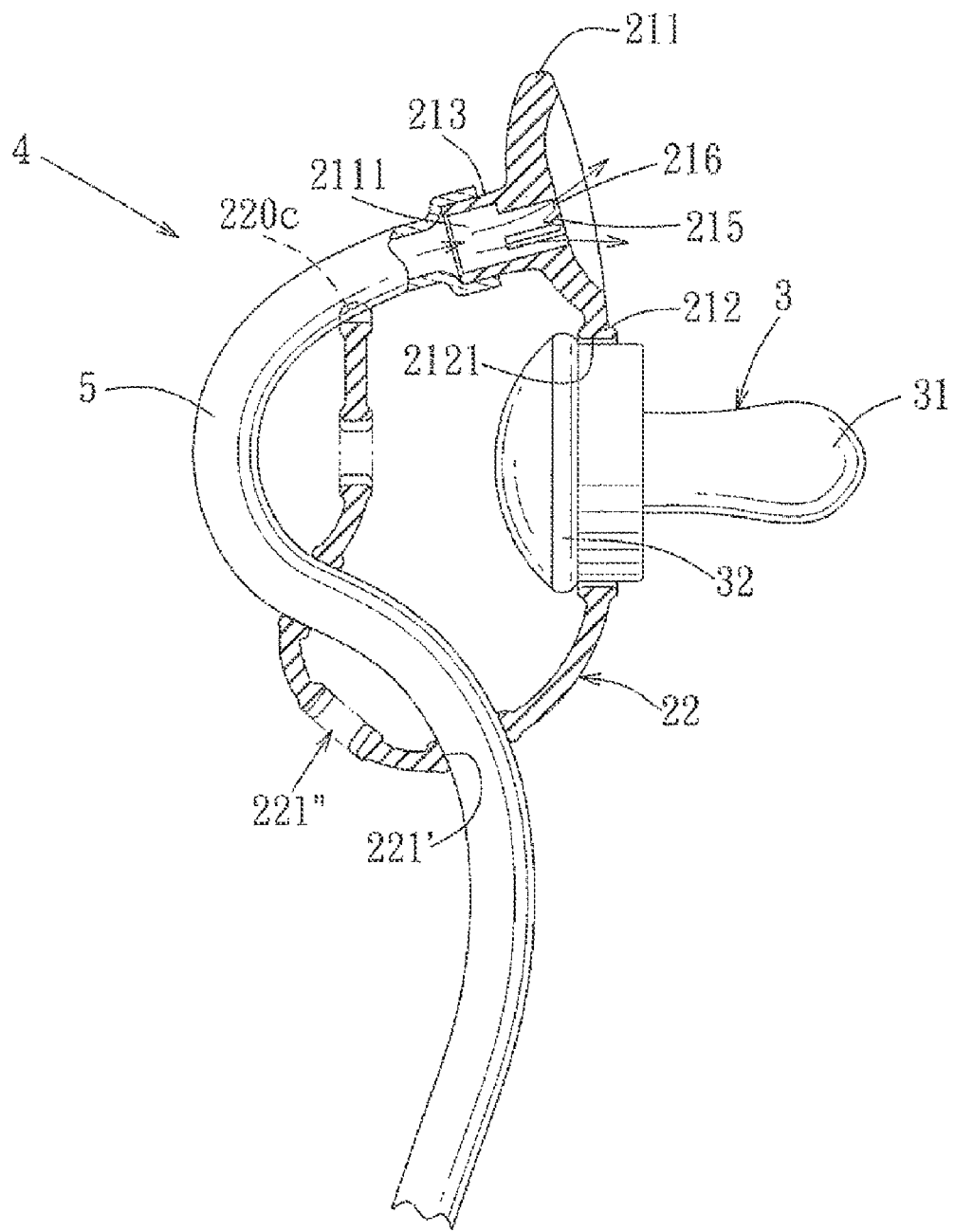
FIG. 6 is a view similar to FIG. 4, but illustrating how a bendable retention plate may be positioned on a delivery tube.

With reference to FIGS. 4 and 6, the delivery tube 5 has one end sleeved fittingly on the tube connector 213 and communicating fluidly with the inlet hole 2111, and the other end adapted to be connected to a source of medication, such as a nebulizer, or a source of gas, such as an oxygen supplying device.

In use, with reference additionally to FIG. 6, the retention plate 22 is bent upwardly so as to abut the bottommost push end (220c) against an upper part of the delivery tube 5 that is proximate to the tube connector 213. Subsequently, a lower part of the delivery tube 5 passes through one of the left and right passage holes 221', 221" that is proximate to the nipple-connecting portion 212 and is clamped thereto, and an intermediate part of the delivery tube 5 passes through another one of the left and right passage holes 221', 221" between said one of the left and right passage holes 221', 221" and the bottommost push end (220c) and is clamped thereto, thereby retaining the retention plate 22 in a bent position. At this time, the delivery tube 5 is pushed by the bottommost push end (220c) to the nose mask portion 211 so that the inlet hole 2111 is disposed close to the infant's or small child's nostrils. Further, when the infant or small child sucks on the nipple portion 31, the nose mask portion 211 is pulled inwardly so that the inlet hole 2111 faces the infant's or small child's nostrils. Hence, the auxiliary device 4 of the present invention does not need adhesive tape to fix the retention plate 22 and the delivery tube 5 onto the face of the infant or small child. During sucking of the nipple portion 31 by the infant or small child, the aerosolized medication or gas is unconsciously inhaled by the infant or small child.

Additionally, through the presence of the flow-damping unit 214 within the inlet hole 2111, a flow current of the aerosolized medication or gas that passes through the inlet hole 2111 into the infant's or small child's nostrils is spread among the hole sections 2112 defined by the central portion 215 and the ribs 216, thereby reducing an impact of the flow current of the aerosolized medication or gas against the infant's or small child's nostrils.

Figure 7:
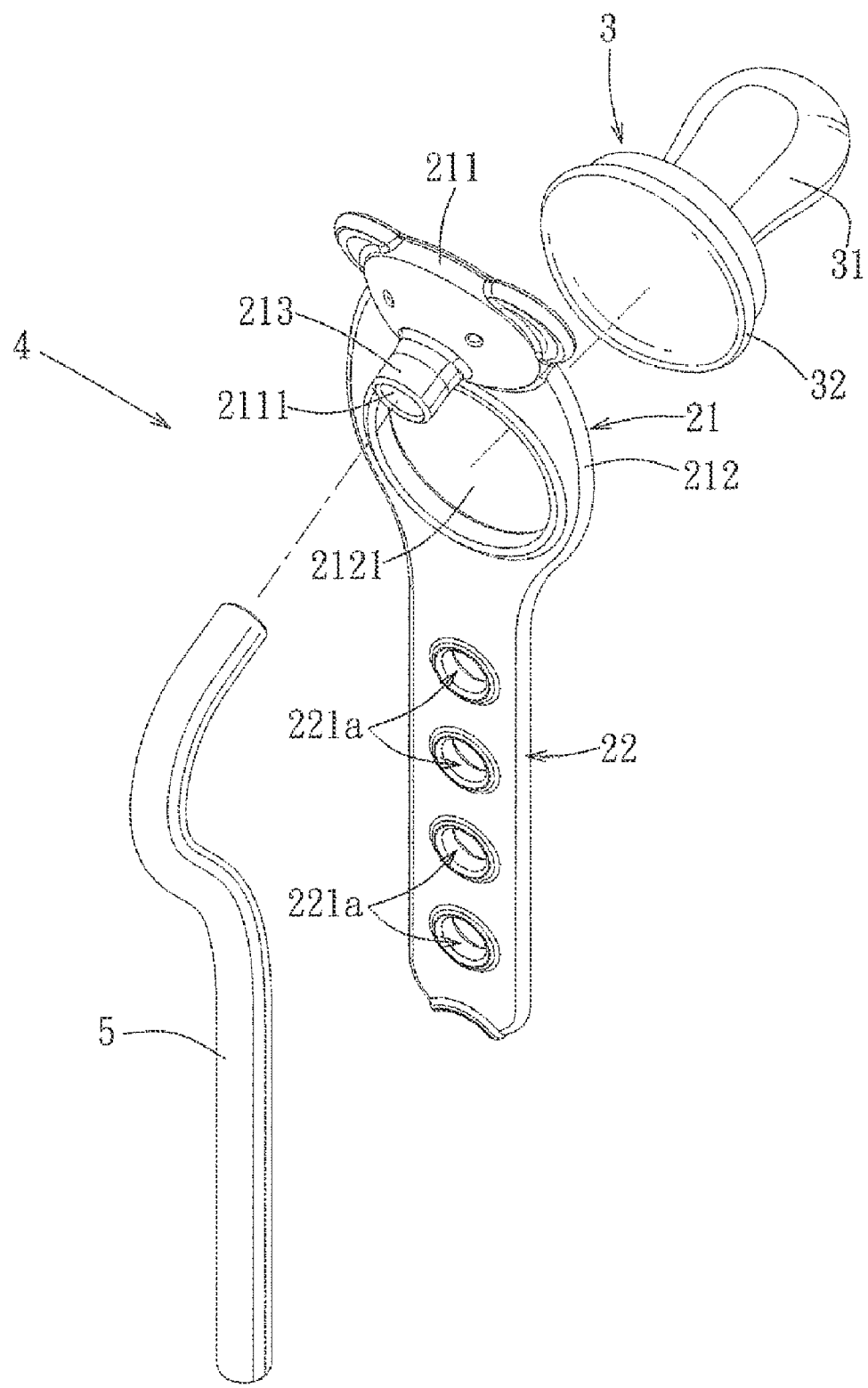
FIG. 7 is an exploded perspective view of an auxiliary device for an aerosol therapy unit according to the second preferred embodiment of this invention.

Referring to FIG. 7, an auxiliary device 4 for an aerosol therapy unit according to the second preferred embodiment of the present invention is shown to be similar to the first preferred embodiment. However, in this embodiment, the passage holes are configured as circular holes (221a). An inner diameter of each circular hole (221a) is smaller than the outer diameter of the delivery tube 5 so as to exert a clamping effect on the delivery tube 5. The advantages of the first preferred embodiment can be similarly achieved using the second preferred embodiment.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

We claim:

1. An auxiliary device for an aerosol therapy unit, comprising:
    a main body including a nose mask portion having a tube connector with an inlet hole, and a nipple-connecting portion connected integrally to said nose mask portion and disposed below said nose mask portion; and
    a delivery tube having one end connected to said inlet hole, and the other end adapted to be connected to a source of medication or gas; and
    a bendable retention plate extending downwardly from said nipple-connecting portion and provided with a plurality of retaining elements that are spaced apart from each other along the length of said retention plate.

2. The auxiliary device of claim 1, further comprising a nipple unit connected detachably to said nipple-connecting portion.

3. The auxiliary device of claim 2, wherein said nipple-connecting portion has a connecting hole for connection with said nipple unit.

4. The auxiliary device of claim 1, wherein said main body further has a flow-damping unit provided transversely within said inlet hole and adapted to dampen a flow current passing through said inlet hole.

5. The aerosol therapeutic device of claim 4, wherein said tube connector has a tube wall confining said inlet hole, said flow-damping unit including a central portion, and a plurality of angularly spaced-apart ribs projecting radially from said central portion to said tube wall.

6. The auxiliary device of claim 1, wherein said retaining elements are configured as passage holes, said delivery tube extending through at least one of said passage holes.

7. The auxiliary device of claim 6, wherein said retention plate has an inner face adapted to face a user, and an outer face opposite to said inner face, said passage holes extending through said inner and outer faces.

8. The auxiliary device of claim 7, wherein said passage holes are circular holes.

9. The auxiliary device of claim 7, wherein said retention plate further has left and right sides, said passage holes including alternating first and second passage holes, said first passage holes opening at said right side, said second passage holes opening at said left side.

10. The auxiliary device of claim 9, wherein each of said first and second passage holes has a large hole portion, and a small hole portion communicating spatially with said large hole portion, said small hole portions of said first passage holes opening at said right side of said retention plate, said small hole portions of said second passage holes opening at said left side of said retention plate, said delivery tube being extendable through said first and second passage holes.

* * * * *